US00PP34246P2

(12) United States Plant Patent
Grazzini

(10) Patent No.: US PP34,246 P2
(45) Date of Patent: May 17, 2022

(54) ***LAGERSTROEMIA* PLANT NAMED 'G18147'**

(50) Latin Name: *Lagerstroemia indica*
Varietal Denomination: G18147

(71) Applicant: Garden Genetics, Bellefonte, PA (US)

(72) Inventor: Richard A. Grazzini, Bellefonte, PA (US)

(73) Assignee: Garden Genetics llc, Bellefonte, PA (US)

( * ) Notice: Subject to any disclaimer, the term of this patent is extended or adjusted under 35 U.S.C. 154(b) by 0 days.

(21) Appl. No.: 17/354,133

(22) Filed: Jun. 22, 2021

(51) Int. Cl.
*A01H 6/00* (2018.01)
*A01H 5/02* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Lagerstroemia* plant named 'G18147' is disclosed, characterized by a clear white flower color, with only slight pink blush to petals under stress. Plants have a dwarf habit with dense branching from the base of the plant and superior Winter hardiness. Foliage is mid-green and shows strong field resistance to powdery mildew. The new variety is a *Lagerstroemia*, normally used for outdoor ornamental purposes.

3 Drawing Sheets

Latin name of the genus and species: *Lagerstroemia indica.*

Variety denomination: 'G18147'.

BACKGROUND OF THE INVENTION

The new *Lagerstroemia* cultivar is a product of a planned breeding program conducted by the inventor at a research nursery in Bellefonte, Pa. The objective of the breeding program was to develop new Crepe Myrtle plants with increased Winter-hardiness. The cross-pollination resulting in this new variety was made during September of 2017.

The seed parent is the unpatented proprietary variety referred to as *Lagerstroemia* '42533-2'. The pollen parent is the unpatented proprietary variety referred to as *Lagerstroemia* '42484-3'. The new variety was selected in July of 2018 by the inventor in a group of seedlings resulting from the 2017 cross-pollination, in a nursery in Bellefonte, Pa.

Asexual reproduction of the new cultivar was performed by softwood cuttings. This was first performed at the same nursery in Bellefonte, Pa. during July of 2018, and has shown that the unique features of this cultivar are stable and reproduced true to type in multiple successive generations.

SUMMARY OF THE INVENTION

The cultivar 'G18147' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G18147'. These characteristics in combination distinguish 'G18147' as a new and distinct *Lagerstroemia* cultivar:

1. Clear white flower color, only slight pink blush to petals under stress.

2. Dwarf habit.
3. Densely-branched from the base of the plant.
4. Superior winter-hardiness.
5. Mid-green foliage with greyed-green veins.
6. Strong field-tolerance to powdery mildew.

PARENT COMPARISON

Plants of the new cultivar 'G18147' are similar to plants of the seed parent in most horticultural characteristics; however, plants of the new cultivar 'G18147' differ in the following:

1. 'G18147' is reliably dwarf in habit; seed parent '42533-2' is tall.
2. 'G18147' has clear white flowers; seed parent '42533-2' frequently displays pink pigment in the flower petals.
3. 'G18147' blooms 7 to 10 days earlier than seed parent '42533-2'.
4. 'G18147' has strong basal branching; seed parent '42533-2' has a much looser branching.
5. 'G18147' blooms heavily and continuously; seed parent '42533-2' has a much shorter period of bloom.

Plants of the new cultivar 'G18147' are similar to plants of the pollen parent in most horticultural characteristics; however, plants of the new cultivar 'G18147' differ in the following:

1. 'G18147' is reliably dwarf in habit; pollen parent is taller.
2. 'G18147' has clear white flowers; pollen parent '42484-3' frequently displays pink pigment in the flower petals.
3. 'G18147' blooms 3 to 5 days earlier than pollen parent '42484-3'.
4. 'G18147' has strong, dense, basal branching; pollen parent '42484-3' has much more open branching.

5. 'G18147' blooms heavily and continuously; pollen parent '42484-3' has a much shorter period of bloom.

COMMERCIAL COMPARISON

Plants of the new cultivar 'G18147' are comparable to the commercial variety *Lagerstroemia* 'G2X13377', U.S. Plant Pat. No. 30,765. The two *Lagerstroemia* varieties are similar in most horticultural characteristics, however, the new variety 'G18147' differs in the following;

1. New variety 'G18147' is dwarf and compact, 75-80 cm tall by 110-120 cm wide. Comparison variety 'G2X13377' is taller and more upright, being about 90 cm tall by 105 cm wide.
2. New variety 'G18147' is more densely branched. Comparison variety 'G2X13377' is more open in habit.
3. New variety 'G18147' has a more pure white flower color Comparison variety 'G2X13377' is frequently tinged with red or pink pigment.
4. Flower display of new variety 'G18147' forms an umbrella-like canopy. Comparison variety 'G2X13377' blooms at the top of its stems.
5. New variety 'G18147' has leaves which are mid-green with grey-green veins. Comparison variety 'G2X13377' has light green foliage.

Plants of the new cultivar 'G18147' are comparable to the commercial variety *Lagerstroemia* 'Black Diamond Pure White', unpatented. The two *Lagerstroemia* varieties are similar in most horticultural characteristics; however, the new variety 'G18147' differs in the following;

1. New variety 'G18147' is a compact shrub, rarely growing more than 30" high. Comparison variety 'Black Diamond Pure White' is a small tree, reaching 10-12 ft tall.
2. New variety 'G18147' has small, mid-green foliage with grey-green veins. Comparison variety 'Black Diamond Pure White' has large, dark violet, almost black leaves.
3. New variety 'G18147' is reliably hardy to USDA zone 6a. Comparison variety 'Black Diamond Pure White' is only hardy to USDA zone 7.
4. Flowers of variety 'G18147' are clear white with an occasional pink blush. Comparison variety 'Black Diamond Pure White' has pure white flowers.

BRIEF DESCRIPTION OF THE PHOTOGRAPHS

The accompanying photograph in FIG. 1 illustrates a typical flowering plant of 'G18147' grown outdoors in Bellefonte, Pa. at approximately 6 months old.

Figure 1:
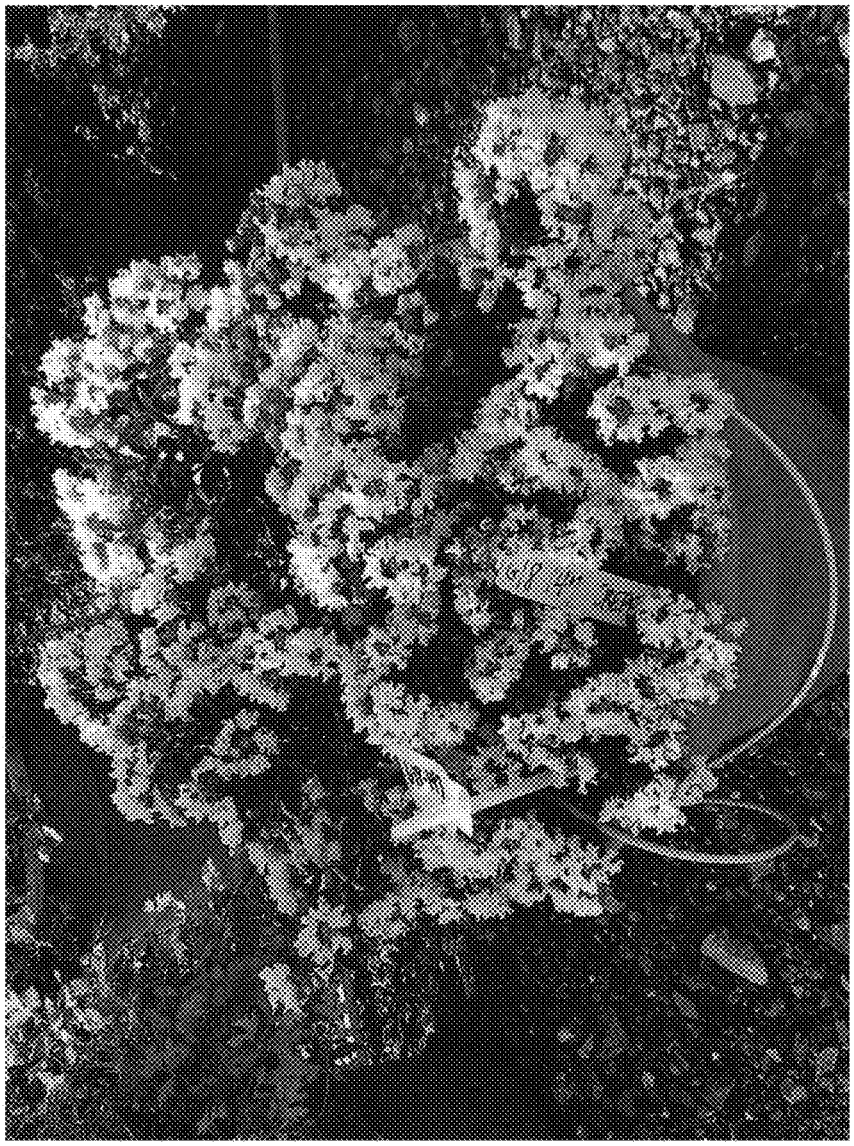
Figure 2:
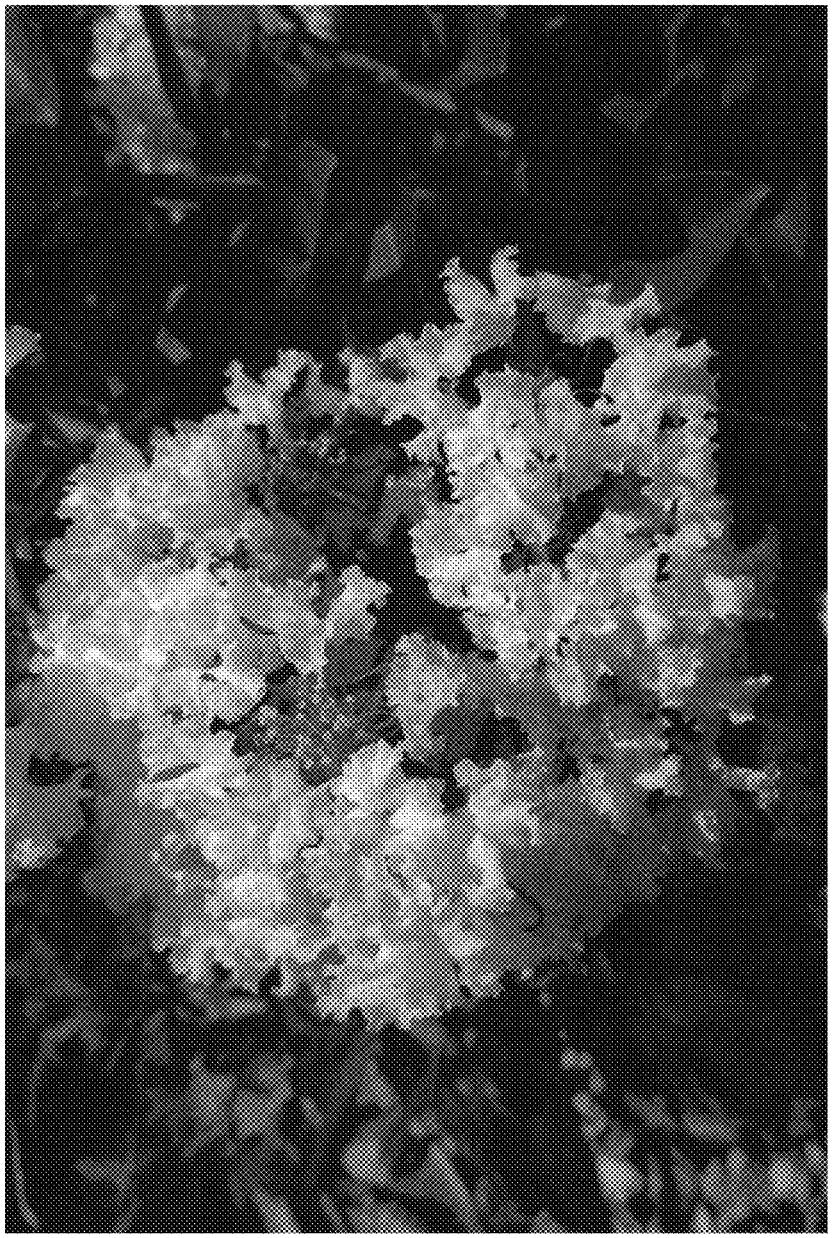
FIG. 2 illustrates a close-up of the inflorescence.
Figure 3:
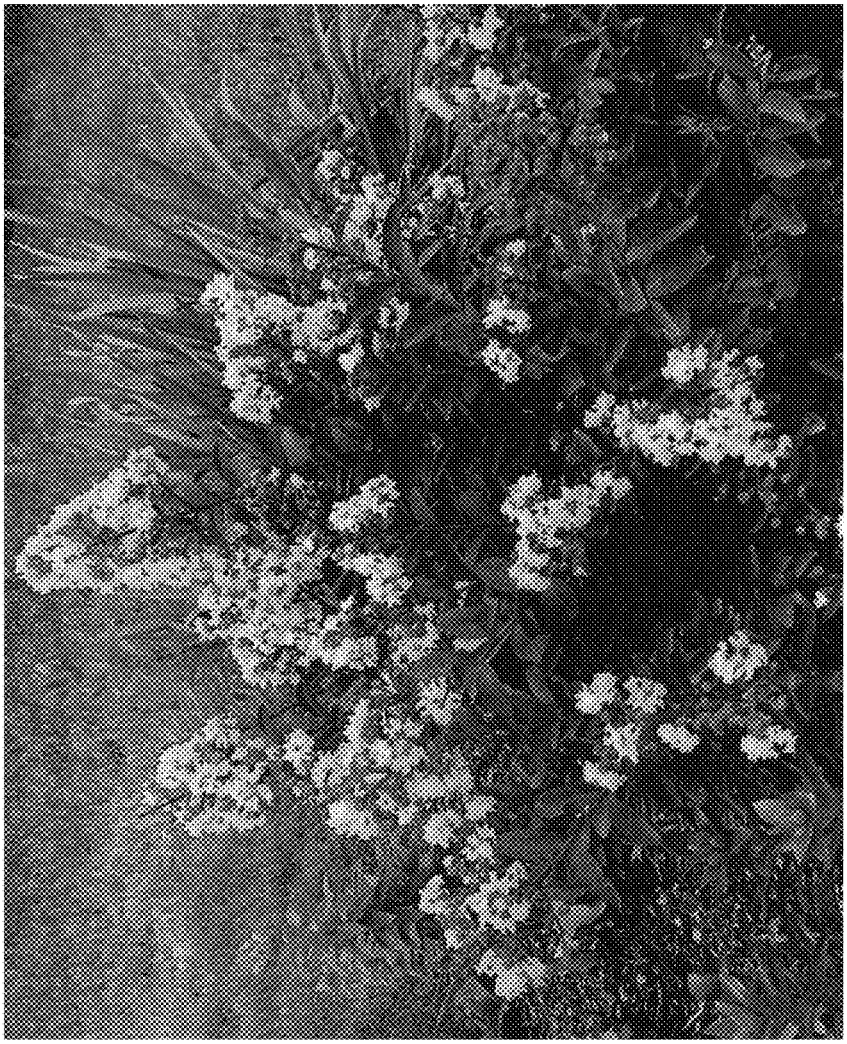
FIG. 3 illustrates a field grown plant at about 6 months.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'G18147' plants grown outdoors in Bellefonte, Pa. The growing temperature ranged from approximately 18° C. to 28° C. during the day and from approximately 6° C. to 12° C. during the night. General light conditions are normal sunlight and numerical values represent averages of typical plant types. Measurements were taken during August of 2019 and August of 2020.

Botanical classification: *Lagerstroemia indica* 'G18147'.

PROPAGATION

Type of propagation typically used: Softwood cuttings.

Time to initiate roots: 10 to 14 days at about 24° C.

Time to produce a rooted cutting: 21 to 28 days at about 24° C.

Root description: Thin fibrous, dense, moderate branching. White in color, not accurately measured with RHS Chart.

PLANT

Age of plant described: About 6 months old from a rooted cutting.

Container size: 3 liter container.

Growth habit: Mounded and upright flowering shrub.

Plant spread: 95 to 110 cm.

Plant height: 60 to 75 cm.

Plant vigor: Strong.

Length of primary lateral branches: 60 cm on average.

Diameter of lateral branches: 8 to 10 mm.

Quantity of lateral branches: About 40.

Stem:

*Color.*—New growth: Near RHS Green 135B. Old growth: Near RHS Grey-Brown 199A.

*Shape.*—Round.

*Strength.*—Strong.

*Aspect angle.*—Mostly upright.

*Texture.*—Pubescent then woody with age.

Internode length: Average 3.0 cm.

Bark peel: Not observed.

FOLIAGE

Leaf:

*Arrangement.*—Sub-opposite or opposite.

*Average length.*—3.5 cm.

*Average width.*—2.0 cm.

*Shape of blade.*—Elliptical.

*Apex.*—Acute.

*Base.*—Obtuse.

*Margin.*—Entire.

*Texture of top surface.*—Smooth to slightly ribbed.

*Texture of bottom surface.*—Smooth with prominent veins.

*Color.*—Young foliage upper side: Near RHS Green 141B. Young foliage under side: Near RHS Green 141C. Mature foliage upper side: Near RHS Green 141A. Mature foliage under side: Near RHS Green 141C. Venation: Type: Pinnate. Mature Venation color upper side: Near RHS Yellow-Green 153A. Mature Venation color under side: Near RHS Greyed-Green 195B. Immature Venation color upper side: Near RHS Greyed-Red 179B. Immature Venation color under side: Near RHS Greyed-Green 195B.

*Petiole.*—Length: 1 mm. Diameter: 1 mm. Texture, upper side: Smooth. Texture, under side: Smooth. Color upper and lower surfaces: Near RHS Greyed-Green 195B.

FLOWER

Natural flowering season: Late June until October.
Inflorescence form: Panicles.
Flowers per inflorescence: About 25 open flowers and 50 buds.
Inflorescence size:
*Width.*—20 cm.
*Height.*—Average 20 cm.
Individual flowers:
*Type.*—Rotate.
*Shape.*—Obovate.
*Habit.*—Whorled outward.
*Diameter.*—4.0 cm.
*Depth.*—2.0 cm.
*Persistence.*—Self-cleaning.
*Fragrance.*—Light floral scent.
Petals:
*Arrangement.*—Whorled.
*Number.*—6.
*Shape.*—Overall irregular orbicular.
*Aspect.*—Undulate.
*Margin.*—Undulate, loosely crenate.
*Tip shape.*—Rounded.
*Base shape.*—Rounded.
*Length.*—1.5 cm.
*Width.*—1.5 cm.
*Texture.*—Upper: Glabrous. Lower: Glabrous.
*Color.*—When opening: Upper surface: Near RHS White N155C. Under surface: Near RHS White N155C. Fully opened: Upper surface: Near RHS White N155D. Under surface: Near RHS White N155D.
Bud:
*Shape.*—Sphere.
*Length.*—7 mm.
*Diameter.*—8 mm.
*Color.*—Near RHS Green 142C.
*Prominence of suture.*—Weak.
Calyx:
*Shape.*—Unguiculate.
*Length.*—11 mm.
*Diameter.*—5 to 10 mm.
Sepals:
*Appearance.*—Glossy.
*Arrangement.*—Rotate, fused.
*Shape.*—Narrowly triangular.
*Tip shape.*—Acute.
*Base shape.*—Obtuse.
*Margin.*—Entire.
*Quantity per flower.*—6.
*Length.*—9 mm.
*Width.*—3.5 mm.
*Margin.*—Entire.
*Texture.*—Inner: Coriaceous, rugose. Outer: Smooth.
*Color.*—Inner: Near RHS Green 142C. Outer: Near RHS Greyed-Green 192A.
Peduncle:
*Length.*—Average 1.0 cm.
*Diameter.*—1 mm.
*Texture.*—Glabrous.
*Color.*—Near RHS Yellow-Green 145B.
*Orientation.*—Upright and outward.
*Strength.*—Strong.
Pedicel:
*Length.*—1.3 cm.
*Diameter.*—8 mm.
*Angle.*—About 45 degrees or less from attachment.
*Strength.*—Good.
*Texture.*—Smooth.
*Color.*—Near Greyed-Red 182A.

REPRODUCTIVE ORGANS

Stamens:
*Number.*—About 30.
*Filament length.*—1 cm.
*Filament color.*—Near White 155D.
Anthers:
*Shape.*—Linear.
*Length.*—1 mm.
*Color.*—Yellow 13A.
*Pollen.*—Sparse, colored near Yellow 13A.
Pistil:
*Number.*—1.
*Length.*—1.5 cm.
Stigma:
*Shape.*—Globular.
*Color.*—Near RHS Orange-Red N34A.
*Ovary color.*—Near RHS Green-Yellow 1D.

OTHER CHARACTERISTICS

Fruits and seeds: Not observed to date.
Disease/pest resistance: Shows good field-tolerance to leaf spots and powdery mildew. The observed resistance to mildew is assumed to be for the pathogen *Erysiphe lagerstroemiae*. Typically leaf spot on *Lagerstroemia* is caused by *Cercospora lythracearum*.
Temperature range: Observed to tolerate a temperature range from about −25° C. to 35° C. Root hardy to −28° C., with plant dying back, but, surviving.

What is claimed is:

1. A new and distinct cultivar of *Lagerstroemia* plant named 'G18147' as herein illustrated and described.

* * * * *